United States Patent
Shirasawa et al.

(10) Patent No.: US 6,329,547 B1
(45) Date of Patent: Dec. 11, 2001

(54) VINYLBENZENE DERIVATIVES

(75) Inventors: Eiichi Shirasawa; Koji Konomi; Masaki Ichikawa, all of Ikoma; Hiroshi Suhara, Osaka, all of (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/701,112

(22) PCT Filed: May 19, 1999

(86) PCT No.: PCT/JP99/02601

§ 371 Date: Nov. 22, 2000

§ 102(e) Date: Nov. 22, 2000

(87) PCT Pub. No.: WO99/61403

PCT Pub. Date: Dec. 2, 1999

(30) Foreign Application Priority Data

May 25, 1998 (JP) .................................................. 10-143307

(51) Int. Cl.$^7$ .................................................. C07C 59/74
(52) U.S. Cl. .................. 562/459; 562/459; 562/434; 562/438; 562/11; 562/24; 560/77; 560/51; 560/23; 558/77; 558/178
(58) Field of Search .................................... 562/459, 434, 562/438, 11; 560/51, 23; 558/178

(56) References Cited

U.S. PATENT DOCUMENTS 4,757,089 7/1988 Epstein .

FOREIGN PATENT DOCUMENTS

60032048 * 8/1983 (JP) .
7-13013 2/1993 (JP) .
97/36860 10/1997 (WO) .

OTHER PUBLICATIONS

Kato Hirotsugu et al; " Antimicrobal Compounds for food Preservation. II. Carbonyl Compounds, Including Aliphatic, and Aromatic Cyclic Compounds"; Shokuhin Eiseigaku Zasshi (1966), 7 (1), 60–61.*

Charbonnel–Jobic, Gaelle et al., "N2S2 tetradentate ligands for soft cationic species: preparation of new ligands of potential interest in nuclear medicine", Bull. Soc. Chim. Fr., 1995, vol. 132, No. 5–6, pp. 624–636.

* cited by examiner

*Primary Examiner*—Gary Geist
*Assistant Examiner*—Farhad Forohar
(74) *Attorney, Agent, or Firm*—Frishauf, Holtz, Goodman, Langer & Chick, P.C.

(57) ABSTRACT

The present invention provides compounds represented by the following general formula [I] and salts thereof, which are useful as therapeutic agents for glaucoma,

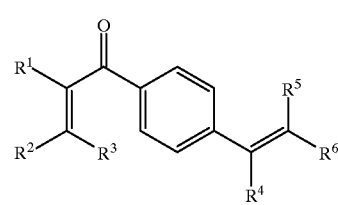

[I]

wherein $R^1$ is H, lower alkyl or phenyl, and the phenyl can be substituted by lower alkyl, hydroxy, lower alkoxy, halogen, nitro or phenyl; $R^2$ and $R^3$, being the same or different, are H, halogen or lower alkyl; $R^4$ and $R^5$, being the same or different, are H, lower alkyl or carboxyl or ester thereof; and $R^6$ is carboxyl or phosphono or ester thereof.

13 Claims, No Drawings

VINYLBENZENE DERIVATIVES

This application is a 371 of PCT/JP99/02601, filed May 19, 1999, now WO 99/61403.

1. Technical Field

The present invention relates to novel compounds which are useful as therapeutic agents for glaucoma.

2. Background Art

In general, glaucoma is a disease wherein visual functions suffer disorders caused by a rise of intraocular pressure. Aqueous humor outflow is closely related to the rise of intraocular pressure. When the aqueous humor outflow is disturbed, the intraocular pressure rises. The aqueous humor flows mainly from trabecular meshwork through a Schlemm's canal outside an eyeball. The aqueous humor outflow can be increased by reducing resistance of the aqueous humor outflow in this trabecular meshwork. Cells which form the trabecular meshwork (trabecular meshwork cells) have sulfhydryl groups. A method of lowering the intraocular pressure has been reported, in which a compound capable of reacting with the sulfhydryl groups is administered so as to make a morphological change in the trabecular meshwork cells and increase the rate of aqueous humor outflow. (Japanese Examined Patent Publication No. 13013/1995). This patent Publication discloses phenoxyacetic acid derivatives, preferably ethacrynic acid as compounds capable of reacting with the sulfhydryl groups.

The method of lowering the intraocular pressure by causing the morphological change in the trabecular meshwork cells is very interesting as a method of treating glaucoma. However, there have not been so many studies of drugs having such a function mechanism yet. A study of creating new drugs in development of therapeutic agents for glaucoma is a very interesting subject.

Accordingly, noting that ethacrynic acid, which is a phenoxyacetic acid derivative having a α,β-unsaturated carbonyl group, has an effect of causing the morphological change in the trabecular meshwork cells and lowering the intraocular pressure, the present inventors synthesized various novel compounds and studied their effects or morphology of the trabecular meshwork cells and intraocular pressure-lowering effects thereof. As a result, the present inventors found that novel vinylbenzene derivatives which have vinylbenzene structure as a basic structure and wherein an α, β-unsaturated carbonyl group is further introduced into their benzene ring have excellent effects. Thus, the present invention has been completed.

DISCLOSURE OF THE INVENTION

The present invention relates to compounds represented by the following general formula [I] and salts thereof (hereinafter referred to as "the present compound" as far as there is no proviso), and pharmaceutical compositions containing them as active ingredients.

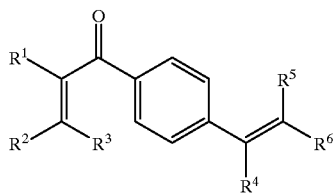

[I]

[wherein $R^1$ is hydrogen, lower alkyl or phenyl, and the phenyl can be substituted by lower alkyl, hydroxy, lower alkoxy, halogen, nitro or phenyl.

$R^2$ and $R^3$, being the same or different, are hydrogen, halogen or lower alkyl.

$R^4$ and $R^5$, being the same or different, are hydrogen, lower alkyl or carboxyl or carboxylate thereof.

$R^6$ is carboxyl or phosphono or ester thereof.]

The groups defined above are described in detail hereinafter.

The lower alkyl is straight-chain or branched alkyl having one to six carbon atoms such as methyl, ethyl, propyl, butyl, hexyl, isopropyl, isobutyl, isopentyl, isohexyl, t-butyl or 3,3-dimethylbutyl.

The lower alkoxy is straight-chain or branched alkoxy having one to six carbon atoms such as methoxy, ethoxy, propoxy, butoxy, hexyloxy, isopropoxy or t-butoxy.

The halogen is fluorine, chlorine, bromine or iodine.

The ester is lower alkyl ester such as methyl ester, ethyl ester, isopropyl ester or hexyl ester, phenyl ester, or phenyl-lower alkyl ester such as benzyl ester or phenethyl ester.

The salts in the present invention can be any pharmaceutically acceptable salts. Examples thereof are salts with an alkali metal or an alkaline earth metal such as sodium, potassium or calcium. When geometrical isomers or optical isomers are present in the present compounds, these isomers are also included in the present invention. The present compounds can be in the form of solvates such as hydrates.

Preferred examples of the present compound are compounds wherein the group(s) are the followings in the compounds represented by the general formula [I];

(1a) $R^1$ is hydrogen, lower alkyl or phenyl, and the phenyl can be substituted by a group selected from lower alkyl, halogen, nitro and phenyl; and/or (2a) ($R^4$ and $R^5$, being the same or different, are hydrogen, lower alkyl or carboxyl.

Namely,

Compounds defined by above (1a) in the compounds represented by the general formula [I], Compounds defined by above (2a) in the compounds represented by the general formula [I], and Compounds defined by a combination of above (1a) and above (2a) in the compounds represented by the general formula [I].

More preferred examples of the present compound are compounds wherein the group(s) are the followings in the compounds represented by the general formula [I];

(1b) $R^1$ is phenyl, and the phenyl can be substituted by a group selected from halogen, nitro and phenyl;

(2b) Both $R^2$ and $R^3$ are hydrogen;

(3b) $R^4$ and $R^5$, being the same or different, are hydrogen or lower alkyl; and/or (4b) $R^6$ is carboxyl.

Namely,

Compounds defined by above (1b) in the compounds represented by the general formula [I], Compounds defined by above (2b) in the compounds represented by the general formula [I], Compounds defined by above (3b) in the compounds represented by the general formula [I], Compounds defined by above (4b) in the compounds represented by the general formula [I], and Compounds defined by any combinations of two or more of above (1b), (2b), (3b) and (4b) in the compounds represented by the general formula [I].

Further preferred examples of the present compound are compounds wherein the group(s) are the followings in the compounds represented by the general formula [I];

(1c) $R^1$ is phenyl, pentafluorophenyl, 4-nitrophenyl or 4-biphenylyl;

(2c) Both $R^2$ and $R^3$ are hydrogen;
(3c) $R^4$ and $R^5$, being the same or different, are hydrogen or methyl; and/or
(4c) $R^6$ is carboxyl.

Namely,

Compounds defined by above (1c) in the compounds represented by the general formula [I], Compounds defined by above (2c) in the compounds represented by the general formula [I], Compounds defined by above (3c) in the compounds represented by the general formula [I], Compounds defined by above (4c) in the compounds represented by the general formula [I], and Compounds defined by any combinations of two or more of above (1c), (2c), (3c) and (4c) in the compounds represented by the general formula [I].

The most preferred specific examples of the present compound are the following compounds and salts thereof.

1) 4-[2-(2, 3, 4, 5, 6-Pentafluorophenyl)acryloyl]cinnamic acid

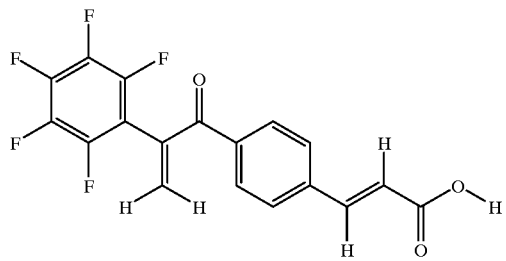

2) 4-[2-(4-Nitrophenyl)acryloyl]cinnamic acid

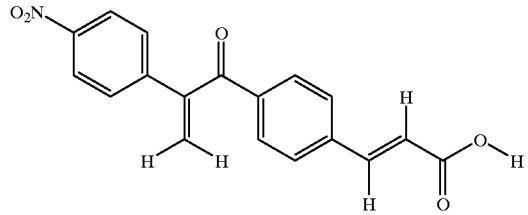

3) 4-(2-Phenylacryloyl)cinnamic acid

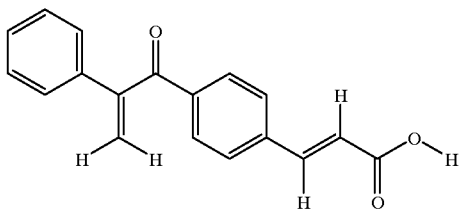

4) α-Methyl-4-(2-phenylacryloyl)cinnamic acid

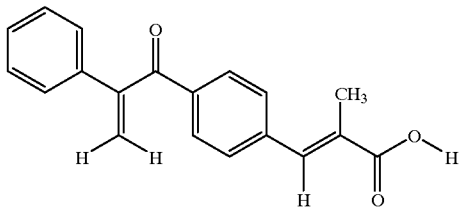

5) β-Methyl-4-(2-phenylacryloyl)cinnamic acid

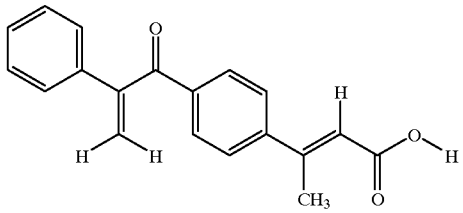

A typical synthesis route scheme of the present compound is shown below.

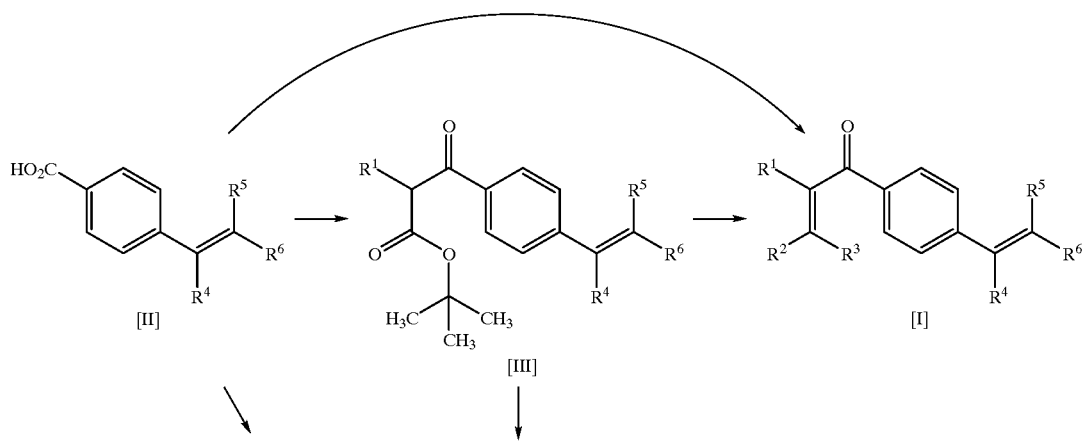

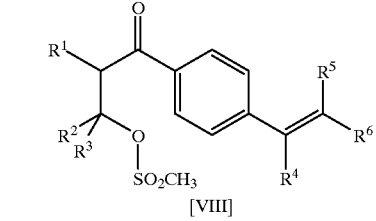

[IV]

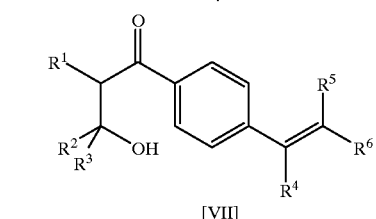

[VIII]

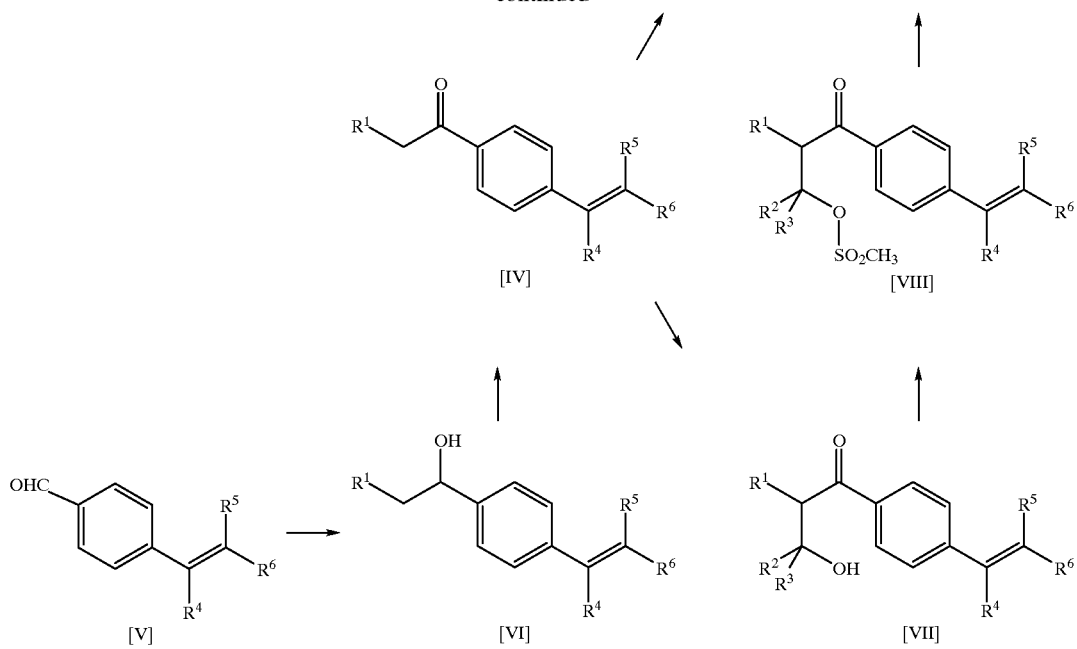

[V]　　[VI]　　[VII]

The present compound [I] can be synthesized by various synthesis routes, for example, as shown in the above reaction route scheme. Each route of this synthetic method is shown below. However, these routes exemplify typical routes and do not represent all methods. Details of specific synthetic methods are described in later Examples.

Route A) [II] → [XVI] → [III] → [IV] → [I]

Route B) [II] → [IV] → [I]

Route C) [V] → [VI] → [IV] → [I]

Route D) [IV] → [VII] → [VIII] → [I]

Route E) [II] → [XVII] → [I]

Synthetic methods of these routes are described in detail below.

Route A) [II] → [XVI] → [IV] → [I]

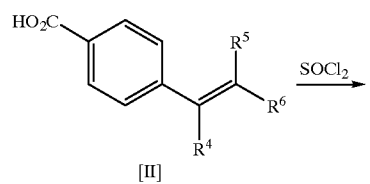

[II]

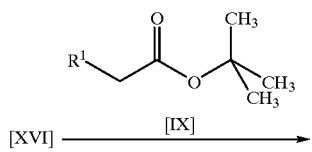

[XVI] —[IX]→

-continued

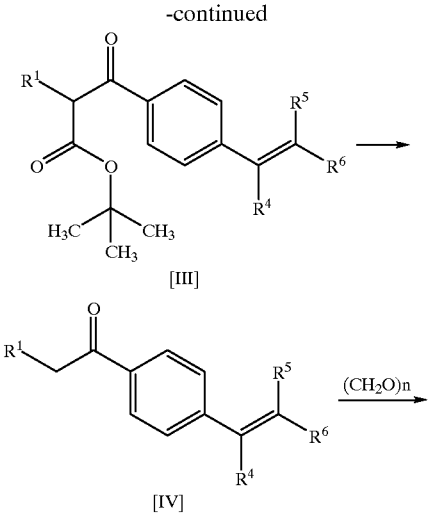

[III]

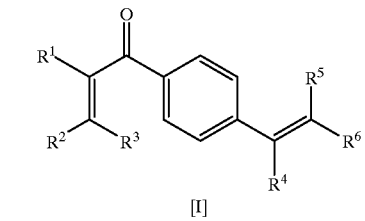

[IV]

[I]

The carboxylic acid derivative [II] is treated with thionyl chloride to convert it into the acid chloride [XVI]. This is reacted with the t-butyl ester derivative [IX] in the presence of a base to convert it into the compounds represented by the formula [III]. The compound [III] is converted into a carboxylic acid in the presence of an acid, and the carboxylic acid is decarboxylated to give the compound represented by the formula [IV]. Then, the compound [IV] is condensed with paraformaldehyde in the presence of a secondary amine by Mannich reaction, and the present compound [I] (wherein $R^2$ and $R^3$ are hydrogen) is obtained by elimination reaction.

Route B) [II] → [XVI] → [IV] → [I]

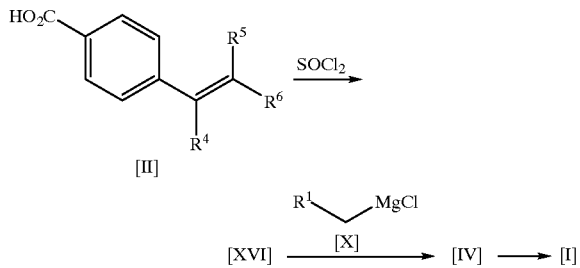

The carboxylic acid derivative [II] is treated with thionyl chloride in the same manner as the route A) to convert is into the acid chloride [XVI]. This is condensed with the Grignard reagent [X] to give the compound [IV]. Then, the present compound [I] (wherein $R^2$ and $R^3$ are hydrogen) is obtained by the same method as the route A).

Route C) [V] → [VI] → [IV] → [I]

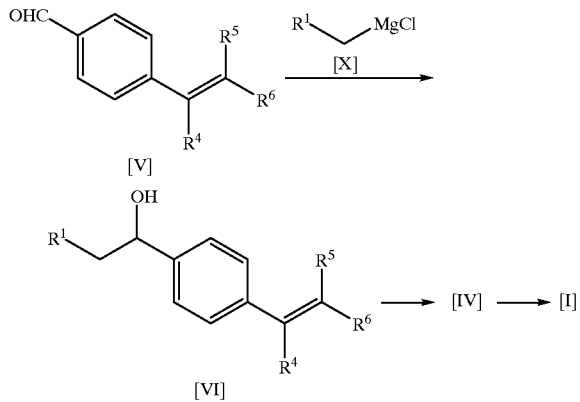

The aldehyde derivative [V] is condensed with the Grignard reagent [X] to convert is into the hydroxy derivative [VI]. The hydroxy derivative is reacted with an oxidizing agent (for example, dimethyl sulfoxide (DMSO)) to give the compound represented by the formula [IV]. Then, the present compound [I] (wherein $R^2$ and $R^3$ are hydrogen) is obtained by the same method as the route A).

Route D) [IV] → [VII] → [VIII] → [I]

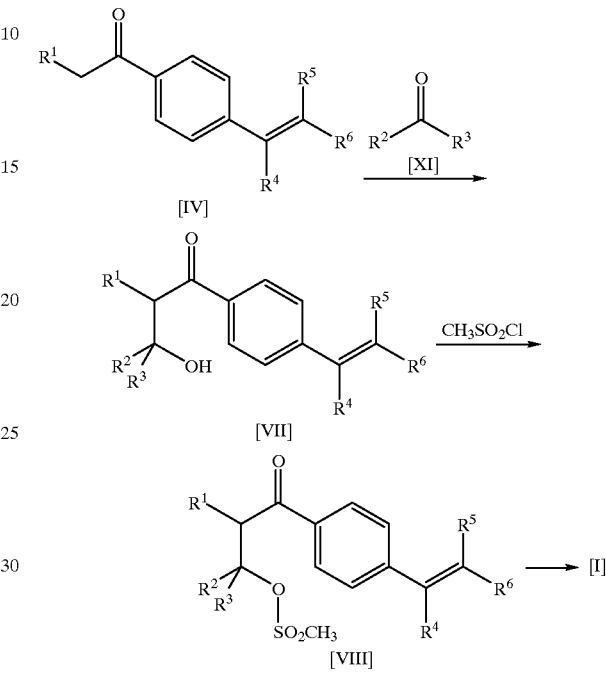

The compound [IV] obtained according to the method of the route A), B) or C) is reacted with the carbonyl compound [XI] in the presence of a base to give the compound represented by the formula [VII]. Then, this is reacted with mesyl chloride to convert it into the mesyloxy derivative [VII]. The mesyloxy derivative [VII] is treated in the presence of a strong base (for example, 1,8-diazabicyclo[5.4.0]-7-undecene (DBU)) to give the present compound [I].

Route E) [II] → [XVII] → [I]

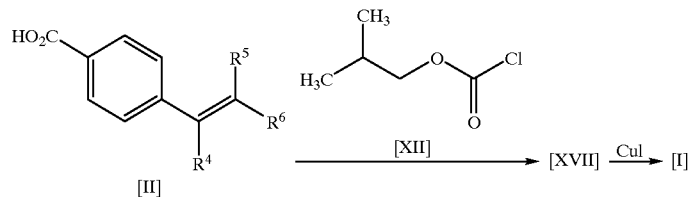

-continued

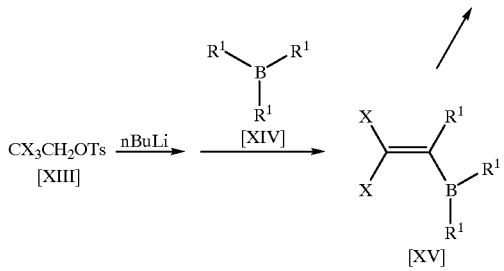

[wherein X is halogen.]

The carboxylic acid derivative [II] is treated with isobutyl chloroformate [XII] to convert is into the mixed acid anhydride [XVII]. Then, the present compound [I] is obtained from this by using a one-pot synthetic method (Tetrahedron Lett., 33, 337–340 (1992)). Namely, the 2, 2, 2-trihaloethyl tosylate [XIII] is treated with n-butyllithium and then reacted with the organoboron compound [XIV] to give the 2, 2-dihalovinylborane derivative [XV]. The borane derivative [XV] is reacted with the above-mentioned mixed acid anhydride [XVII] in the presence of copper(I) iodide without isolating the borane derivative [XV] to give the present compound [I] (wherein $R^2$ and $R^3$ are halogen).

When the reactants have a hydroxy group in their molecule in the above-mentioned synthetic methods, the group can be protected with a suitable protecting group, if necessary, and the protecting group can also be removed by a conventional method after the reaction. When the reactants have a carboxyl group or a phosphono group in their molecule, the carboxyl group or the phosphono group can be esterified, if necessary, and the ester can also be converted into a carboxylic acid or a phosphonic acid by hydrolysis.

The present compounds are novel compounds which are unknown in literatures, and are characterized in that the present compounds have a vinylbenzene structure, of which benzene ring has a double bond substituent, as basic structure, and the benzene ring is further substituted by an α, β-unsaturated carbonyl group.

As described above in the part of "Background Art", it was reported that ethacrynic acid has an effect of lowering intraocular pressure by making a morphological change in trabecular meshwork cells and increasing the rate of aqueous humor outflow (Japanese Examined Patent Publication No. 13013/1995). Ethacrynic acid is a phenoxyacetic acid derivative having an α, β-unsaturated carbonyl group. Focusing attention on this chemical structure of ethacrynic acid, the present inventors studied precisely and found that novel compounds exhibiting higher effects are obtained by introducing one more double bond as a substituent of a benzene ring of ethacrynic acid.

Administration methods of drugs can be a method of administering active compounds themselves or a method of administering the drugs in the form to be decomposed in vivo and to be converted into the active compounds, namely in the form of prodrugs. Both are widely used. The present compounds also have a carboxylic acid group or a phosphonic acid group in their molecule. The present compounds can be administered in the form of the carboxylic acid or the phosphonic acid and also in the form of an ester which can be converted into the carboxylic acid or the phosphonic acid by hydrolysis. When the present compounds have a hydroxy group in their molecule, the present compounds can be administered with the hydroxy group protected with a suitable protecting group.

In order to study utility of the present compounds, effects of the present compounds on morphology of the trabecular meshwork cells and effects of the present compounds on intraocular pressure were investigated. Details will be described later in the part of "Pharmacological Test", and morphological changes of the trabecular meshwork cells by adding the present compounds were studied by image analysis. As a result, the present compounds exhibited excellent cell morphology change effects on the trabecular meshwork cells.

Furthermore, intraocular pressure-lowering effects of the present compounds were directly studied. Namely, effects of the present compounds on intraocular pressure were studied by injecting it into anterior chambers of normal animals and by instillation using laser-induced high intraocular pressure animal models. As a result, the present compounds exhibited excellent intraocular pressure-lowering effects.

The present compound is mainly administered parenterally and can also be administered orally. Examples of dosage forms are eyedrops, injections, tablets, capsules, granules and the like. The present compound can be formulated into preparations by conventional methods. For example, eyedrops can be produced, if necessary, by adding isotonic agents such as sodium chloride and concentrated glycerine; buffers such as sodium phosphate and sodium acetate; surfactants such as polyoxyethylenesorbitan monooleate, polyoxyl 40 stearate and polyoxyethylene hardened castor oil; stabilizers such as sodium citrate and the disodium edetate; preservatives such as benzalkonium chloride and paraben; and the like. pH can be in a range acceptable for ophthalmic preparations, and it is preferably in a range of 4 to 8. Oral preparations such as tablets, capsules and granules can be produced, if necessary, by adding diluents such as lactose, starch, crystalline cellulose and vegetable oil; lubricants such as magnesium stearate and talc; binders such as hydroxypropylcellulose and polyvinyl pyrrolidone; disintegrators such as calcium carboxymethylcellulose; coating agents such as hydroxypropylmethylcellulose, macrogol and silicone resin; and gelatin film-forming agents.

The dosage of the present compound can be selected suitably depending on symptoms, age, dosage form and the like. In the case of the eyedrops, the concentration is 0.001 to 3% (w/v), and one to several drops can be instilled per day. In the case of the oral preparation, the usual daily dosage is 1 to 1000 mg, which can be given in one or a few divided doses.

Preparations, formulations and results of pharmacological tests of the present compounds are shown below. These examples do not limit the scope of the present invention, but are intended to make the present invention more clearly understandable.

BEST MODE FOR CARRYING OUT THE INVENTION

PREPARATION OF COMPOUNDS

REFERENCE EXAMPLE 1 t-Butyl (2, 3, 4, 5, 6-pentafluorophenyl)acetate (Reference compound No. 1—1)

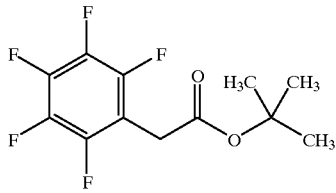

To isobutene (4 ml) are added (2, 3, 4, 5, 6-pentafluorophenyl)acetic acid (3.0 g), ether (1 ml) and concentrated sulfuric acid (0.07 ml) under a nitrogen atmosphere and dry ice cooling, and the mixture is stirred in a pressure tube at room temperature for three days. The reaction mixture cooled with dry ice is added to a mixture of a 10% aqueous sodium hydrogencarbonate solution and ice. The whole is stirred and then extracted with either. The organic layer is washed with saturated brine, dried over anhydrous magnesium sulfate and concentrated under reduced pressure to give 3.10 g (83%) of the titled compound
(Reference compound No. 1—1)
(Reference compound No. 1—1)
 IR (Film, cm$^{-1}$) 2983, 2940, 1740, 1658, 1510, 1371, 1307, 1159, 981

The following compounds are obtained by a method similar to Reference Example 1.

t-Butyl (4-nitrophenyl)acetate (Reference compound No. 1–s)
 IR (Film, cm$^{-1}$) 2979, 1731, 1607, 1521, 1369, 1347, 1231, 1147 t-Butyl (4-biphenylyl)acetate (Reference compound No. 1–3)
 mp 44.5–48.5° C.
 IR (KBr, cm$^{-1}$) 3028, 2976, 1730, 1602, 1486 t-Butyl (4-tolyl)acetate (Reference compound No. 1–4)

t-Butyl (4-fluorophenyl)acetate (Reference compound No. 1–5)

t-Butyl (4-chlorophenyl)acetate (Reference compound No. 1–6)

REFERENCE EXAMPLE 2

Ethyl 4-carboxycinnamate (Reference compound No. 2-1)

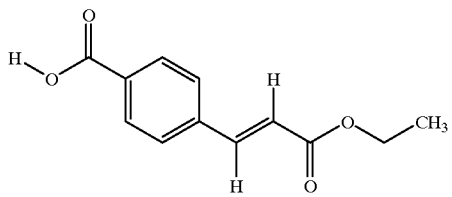

To a solution of 4-formylbenzoic acid (10 g) in pyridine (68 ml) are added ethyl malonate monopotassium salt (23 g), p-toluenesulfonic acid monohydrate (25 g) and piperdine (0.99 ml). The mixture is heated gradually and then stirred at 120° C. for 1.5 hours. Under ice cooling, 2 N hydrochloric acid is added to the reaction mixture to acidify it, and the resulting precipitate is filtered off to give 11.7 g (79%) of the titled compound (Reference compound No. 2-1) as crystals.
(Reference compound No. 2-1)
 mp 194.5–197.0° C.
 IR (KBr, cm$^{-1}$) 2981, 1711, 1687, 1609, 1569, 1511, 847

The following compounds are obtained by a method similar to Reference Example 2.

Ethyl 4-carboxy-α-methylcinnamate (Reference compound No. 2—2)
 mp 145–149° C.
 IR (KBr, cm$^{-1}$) 2985, 1707, 1678, 1425, 1293, 1259, 1203, 1125, 771 t-Butyl 4-carboxycinnamate (Reference compound No. 2–3)
 mp 210° C. (decomp.)
 IR (KBr, cm$^{-1}$) 2979, 1707, 1678, 1639, 1608, 1567, 1294, 1254, 1202, 1156, 964

REFERENCE EXAMPLE 3

Ethyl 4-carboxy-β-methylcinnamate (Reference compound No. 3-1)

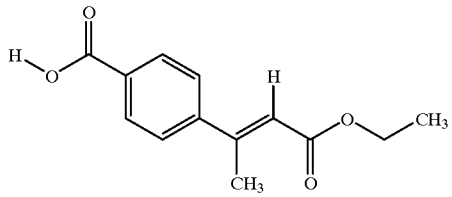

1) To a solution of 4-acetylbenzoic acid (3.9 g) in anhydrous methylene chloride (120 ml) are added 4-dimethylaminopyridine (1.5 g), t-butyl alcohol (4.6 ml), N-methylmorpholine (3.4 ml) and 1-ethyl-3-(3-dimethylaminopropyl)carbodiimide hydrochloride (6.0 g) under ice cooling. The mixture is stirred under ice cooling for six hours and under water cooling overnight. The reaction mixture is concentrated under reduced pressure, water is added to the concentrate, and the whole is extracted with ether. The organic layer is washed with saturated brine, dried over anhydrous magnesium sulfate and concentrated under reduced pressure. The residue is purified by silica gel column chromatography to give 3.13 g (59%) of t-butyl 4-acetylbenzoate as crystals.
 mp 57.5–58.8° C.
 IR (KBr, cm$^{-1}$) 3350, 2986, 2934, 1708, 1682, 1503

2) A solution of triethyl phosphonoacetate (0.98 ml) in anhydrous tetrahydrofuran (4 ml) is added dropwise to a solution of sodium hydride (60%, oily) (220 mg) in anhydrous tetrahydrofuran (15 ml) under a nitrogen atmosphere and ice cooling, and the mixture is stirred under ice cooling for 10 minutes. Then, a solution of t-butyl 4-acetylbenzoate (1.0 g) in anhydrous tetrahydrofuran (4 ml) is added dropwise to the mixture, stirring it at room temperature overnight. Ether is added to the reaction mixture under ice cooling, and the whole is extracted. The organic layer is washed with a 10% aqueous citric acid solution, water and saturated brine successively, dried over anhydrous magnesium sulfate and concentrated under reduced pressure. The residue is purified by silica gel column chromatography to give 0.76 g (58%) of ethyl 4-(t-butoxycarbonyl)-β-methylcinnamate.

IR (Film, cm$^{-1}$) 2979, 2934, 1713, 1631, 1567, 1455, 1169, 1115

3) Ethyl 4-(t-butoxycarbonyl)-β-methylcinnamate (755 mg) is dissolved in a 4 N solution of hydrogen chloride in ethyl acetate (6.5 ml), and the solution is stirred at room temperature for 18 hours. The reaction mixture is concentrated under reduced pressure, isopropyl ether is added to the concentrate, and the resulting precipitate is filtered off to give 550 mg (90%) of the titled compound (Reference compound No. 3-1) as crystals.

(Reference compound No. 3-1)

mp 160.0–161.7° C.

IR (KBr, cm$^{-1}$) 2979, 2668, 2543, 1712, 1689, 1626, 1565, 1424, 1367

REFERENCE EXAMPLE 4

Diethyl 2-(4-formylphenyl)maleate (Reference compound No. 4-1)

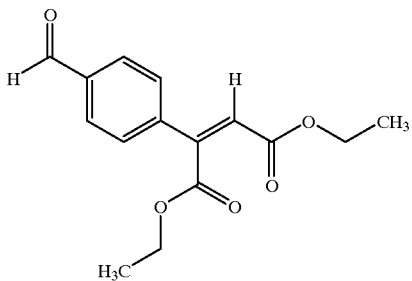

1) A 1.0 M solution of 4-tolylmagnesium bromide in ether (20.5 ml) is added dropwise to a solution of diethyl oxalate (6.5 g) in anhydrous tetrahydrofuran (41 ml) under a nitrogen atmosphere and ice cooling. Five minutes after completing the addition, the mixture is stirred at room temperature for 1.5 hours. To the reaction mixture is added 1 N hydrochloric acid, and the whole is extracted with ether. The organic layer is washed with water and saturated brine successively, dried over anhydrous magnesium sulfate and concentrated under reduced pressure. The resulting residue is purified by silica gel column chromatography to give 2.99 g (76%) of ethyl 4-tolylglyoxylate.

IR (Film, cm$^{-1}$) 2984, 1736, 1684, 1606, 1307, 1203, 1176, 1015

2) A solution of diethyl ethoxycarbonylmethylphosphonate (3.3 g) in anhydrous tetrahydrofuran (20 ml) is added dropwise to a suspension of sodium hydride (60%, oily) (676 mg) in anhydrous tetrahydrofuran (30 ml) under a nitrogen atmosphere and ice cooling, and further a solution of ethyl 4-tolylglyoxylate (2.96 g) in anhydrous tetrahydrofuran (22 ml) is added dropwise thereto. The mixture is stirred at room temperature for 30 minutes, a 10% aqueous citric acid solution is added to the reaction mixture, and the whole is extracted with ether. The organic layer is washed with water and saturated brine successively, dried over anhydrous magnesium sulfate and concentrated under reduced pressure. The resulting residue is purified by silica gel column chromatography to give 3.57 g (88%) of diethyl 2-(4-tolyl)maleate.

IR (Film, cm$^{-1}$) 2982, 1732, 1714, 1623, 1608, 1372, 1288, 1205, 1176, 1033

3) To a solution of diethyl 2-(4-tolyl)maleate (1.5 g) in carbon tetrachloride (29 ml) are added N-bromosuccinimide (3.1 g) and 2,2'-azobis(isobutyronitrile) (45 mg), and the mixture is refluxed for two days. The reaction mixture is concentrated under reduced pressure, a 10% aqueous sodium hydrogencarbonate solution is added to the concentrate, and the whole is extracted with ether. The organic layer is washed with water and saturated brine successively, dried over anhydrous magnesium sulfate and concentrated under reduced pressure. The residue is purified by silica gel column chromatography to give 1.15 g (56%) of diethyl 2-[4-(dibromomethyl)phenyl]maleate as crystals.

mp 89.0–92.5° C.

IR (KBr, cm$^{-1}$) 3029, 2991, 1714, 1626, 1372, 1342, 1295, 1186, 1026, 847

4) A solution of silver nitrate (607 mg) in water (5 ml) is added to a solution of diethyl 2-[4-(dibromomethyl)phenyl]maleate (500 mg) in 2-methoxyethanol (15 ml) under a nitrogen atmosphere, and the mixture is stirred for 25 minutes while heating it at 95° C. Under ice cooling, 0.1 N hydrochloric acid is added to the reaction mixture, and the whole is extracted with ethyl acetate. The organic layer is washed with water and saturated brine successively, dried over anhydrous magnesium sulfate and concentrated under reduced pressure. The residue is purified by silica gel column chromatography to give 280 mg (85%) of the titled compound (Reference compound No. 4-1).

(Reference compound No. 4-1)

IR (Film, cm$^{-1}$) 2983, 1722, 1626, 1372, 1343, 1283, 1209, 1180

REFERENCE EXAMPLE 5

Diethyl (E)-2-(4-carboxyphenyl)vinylphosphonate (Reference compound No. 5-1)

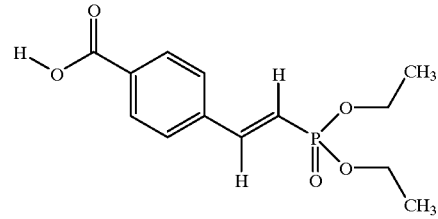

1) Anhydrous potassium carbonate (4.7 g) is added to a solution of terephthalaldehydic acid (5.1 g) in anhydrous dimethylformamide (110 ml), and the mixture is stirred at room temperature for 10 minutes. Then, methyl iodide (2.5 ml) is added thereto, and the mixture is stirred overnight. Water is added to the reaction mixture, and the whole is extracted with ethyl acetate. The organic layer is washed with water and saturated brine successively, dried over anhydrous sodium sulfate and concentrated under reduced pressure. The resulting residue is purified by silica gel column chromatography to give 4.7 g (84%) of methyl 4-formylbenzoate as crystals.

mp 58.9–60.5° C.

IR (KBr, cm$^{-1}$) 3021, 1728, 1684, 1578, 1435, 1392

2) A 1.0 M solution of lithium bis(trimethylsilyl)amide in tetrahydrofuran (17 ml) is diluted with anhydrous tetrahydrofuran (81 ml) under a nitrogen atmosphere and dry ice cooling, and then a solution of tetraethyl methylenebis(phosphonate) (4.6 g) in anhydrous tetrahydrofuran (8 ml) is added dropwise thereto. The mixture is stirred under dry ice cooling for 30 minutes, and then a solution of methyl 4-formylbenzoate (2.64 g) in anhydrous tetrahydrofuran (12 ml) is added dropwise thereto. The mixture is stirred under dry ice cooling for 1.5 hours and further under ice cooling for 2.5 hours. Ethyl acetate is added to the reaction mixture. The organic layer is washed with water and saturated brine successively, dried over anhydrous sodium sulfate and concentrated under reduced pressure. The resulting precipitate is filtered off to give 4.1 g (86%) of diethyl (E)-2-[4-(methoxycarbonyl)phenyl] vinylphosphonate as crystals.

mp 60–65° C.

IR (KBr, cm$^{-1}$) 3003, 1720, 1620, 1568, 1433, 1236

3) Diethyl (E)-2-[4-(methoxycarbonyl)phenyl] vinylphosphonate (4.0 g) is dissolved in a mixed solvent of ethanol (26 ml)-tetrahydrofuran (13 ml). Then, a 1 N aqueous sodium hydroxide solution (15 ml) is added thereto, and the mixture is stirred at room temperature for 24 hours. A 10% aqueous citric acid solution is added to the reaction mixture to acidify it, and the whole is extracted with ethyl acetate. The organic layer is washed with water and saturated brine successively, dried over anhydrous sodium sulfate and concentrated under reduced pressure. The resulting precipitate is filtered off to give 3.4 g (89%) of the titled compound (Reference compound No. 5-1) as crystals.

(Reference compound No. 5-1)

mp 135.0–136.5° C.

IR (KBr, cm$^{-1}$) 2990, 1707, 1570, 1480, 1240

EXAMPLE 1

Ethyl 4-[(2RS)-2-(t-butoxycarbonyl)-2-(2,3,4,5,6-pentafluorophenyl)acetyl]cinnamate (Compound No. 1-1)

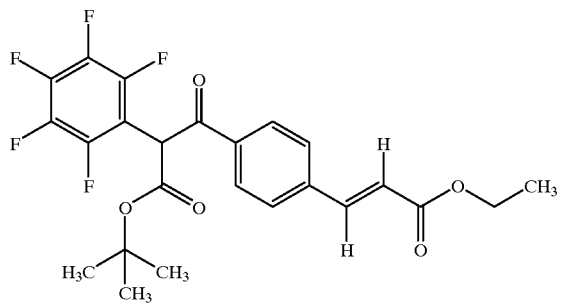

Thionyl chloride (2.8 ml) is added dropwise to a solution of ethyl 4-carboxycinnamate (Reference compound No. 2-1, 1.7 g) in chloroform (5 ml) under a nitrogen atmosphere. Then, dimethylformamide (one drop) is added thereto, and the mixture is refluxed for 30 minutes. The reaction mixture is concentrated under reduced pressure to give the corresponding acid chloride.

A 0.5 M solution of potassium bis(trimethylsilyl)amide in toluene (18 ml) is added dropwise to a solution of t-butyl (2,3,4,5,6-pentafluorophenyl)acetate (Reference compound No. 1-1, 2.17 g) in tetrahydrofuran (20 ml) under a nitrogen atmosphere and dry ice cooling. After five minutes, furthermore, a solution of the above-mentioned acid chloride in tetrahydrofuran (20 ml) is added dropwise thereto. Twenty minutes after completing the addition, the mixture is stirred at room temperature for 1.5 hours. A 10% aqueous citric acid solution is added to the reaction mixture, and the whole is extracted with ether. The organic layer is washed with water and saturated brine successively, dried over anhydrous magnesium sulfate and concentrated under reduced pressure. The resulting residue is purified by silica gel column chromatography to give 526 mg (12%) of the titled compound (Compound No. 1-1) as crystals.

(Compound No. 1-1)

mp 87.5–88.5° C.

IR (KBr, cm$^{-1}$) 2979, 1716, 1637, 1522, 1496, 1373, 1177

The following compounds are obtained by a method similar to Example 1.

Ethyl 4-[(2RS)-2-(t-butoxycarbonyl)-2-(4-nitrophenyl) acetyl]cinnamate (Compound No. 1-2)

IR (Film, cm$^{-1}$) 2980, 1715, 1639, 1603, 1523, 1368, 1348, 1278, 1148

Ethyl 4-[(2RS)-2-(t-butoxycarbonyl)-2-(4-biphenylyl) acetyl]cinnamate (Compound No. 1-3)

IR (Film, cm$^{-1}$) 2980, 1713, 1639, 1603, 1486

Ethyl 4-[(2RS)-2-(t-butoxycarbonyl)-2-(4-tolyl)acetyl] cinnamate (Compound No. 1-4)

Ethyl 4-[(2RS)-2-(t-butoxycarbonyl)-2-(4-fluorophenyl) acetyl]cinnamate (Compound No. 1-5)

Ethyl 4-[(2RS)-2-(t-butoxycarbonyl)-2-(4-chlorophenyl) acetyl]cinnamate (Compound No. 1-6)

EXAMPLE 2

4-[(2,3,4,5,6-Pentafluorophenyl)acetyl]cinnamic acid (Compound No. 2-1)

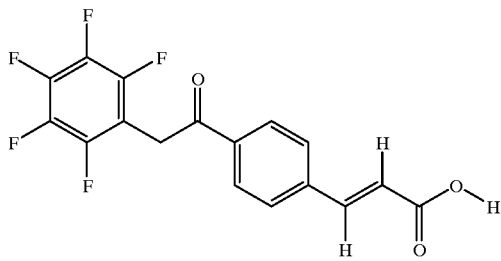

Into a pressure tube is introduced a solution of ethyl 4-[(2RS)-2-(t-butoxycarbonyl)-2-(2,3,4,5,6-pentafluorophenyl)acetyl]cinnamate (Compound No. 1-1, 500 mg) in dioxane (2 ml), and concentrated sulfuric acid (2 ml) is added thereto. The mixture is stirred for four hours while heating it at 130° C. The reaction mixture is cooled with ice, and the resulting precipitate is filtered off to give 256 mg (70%) of the titled compound (Compound No. 2-1) as crystals.

(Compound No. 2-1)

mp 228–234° C.

IR (KBr, cm$^{-1}$) 2975, 1673, 1526, 1502, 1307, 1280

The following compounds are obtained by a method similar to Example 2.

4-[(4-Nitrophenyl)acetyl]cinnamic acid (Compound No. 2-2)

mp 247–251° C.

IR (KBr, cm$^{-1}$) 2895, 1683, 1628, 1601, 1518, 1343, 1228, 991

4-[(4-Biphenylyl)acetyl]cinnamic acid (Compound No. 2-3)

mp 250° C. or higher

IR (KBr, cm$^{-1}$) 3030, 1682, 1631, 1600, 1558, 1487

4-[(4-Tolyl)acetyl]cinnamic acid (Compound No. 2-4)

4-[(4-Fluorophenyl)acetyl]cinnamic acid (Compound No. 2-5)

4-[(4-Chlorophenyl)acetyl]cinnamic acid (Compound No. 2-6)

EXAMPLE 3

Ethyl 4-(phenylacetyl)cinnamate (Compound No. 3-1)

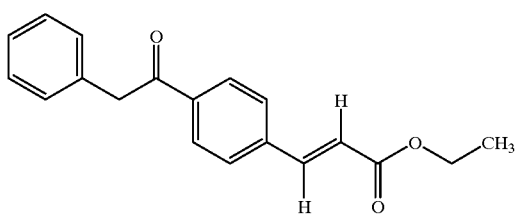

Thionyl chloride (3.3 ml) is added dropwise to a solution of ethyl 4-carboxycinnamate (Reference compound No. 2-1, 2.0 g) in chloroform (4 ml) under a nitrogen atmosphere, then dimethylformamide (one drop) is added to the solution, and the mixture is refluxed for 30 minutes. The reaction mixture is concentrated under reduced pressure to give a residue of the corresponding acid chloride. The residue is dissolved in tetrahydrofuran (30 ml) under a nitrogen atmosphere, and the solution is cooled with dry ice. A 2.0 M solution of benzylmagnesium chloride in tetrahydrofuran (4.5 ml) is added dropwise thereto. Twelve minutes after completing the addition, a 10% aqueous citric acid solution is added to the reaction mixture under dry ice cooling, then the temperature is raised to room temperature, and the whole is extracted with ether. The organic layer is washed with water and saturated brine successively, dried over anhydrous magnesium sulfate and concentrated under reduced pressure. The resulting residue is purified by silica gel column chromatography to give 685 mg (26%) of the titled compound (Compound No. 3-1) as crystals.

(Compound No. 3-1)

mp 110.5–111.3° C.

IR (KBr, cm$^{-1}$) 2986, 1690, 1410, 1330, 1206, 970, 704

The following compounds are obtained by a method similar to Example 3.

Ethyl 4-(n-butyryl)cinnamate (Compound No. 3-2)
mp 51.7–53.9° C.
IR (KBr, cm$^{-1}$) 2963, 1770, 1680, 1603, 1561, 1472, 1371, 999
Ethyl α-methyl-4-(phenylacetyl)cinnamate (Compound No. 3-3)
mp 35.5–37.8° C.
IR (KBr, cm$^{-1}$) 2983, 1706, 1683, 1602, 1452, 1254, 1112
Ethyl β-methyl-4-(phenylacetyl)cinnamate (Compound No. 3-4)
mp 81.7–83.0° C.
IR (KBr, cm$^{-1}$) 3040, 2982, 1713, 1683, 1624, 1601, 1478, 1268, 1225
Ethyl 4-propionylcinnamate (Compound No. 3-5)
Ethyl 4-isovalerylcinnamate (Compound No. 3-6)
Ethyl 4-acetylcinnamate (Compound No. 3-7)

EXAMPLE 4

4-(Phenylacetyl)cinnamic acid (Compound No. 4-1)

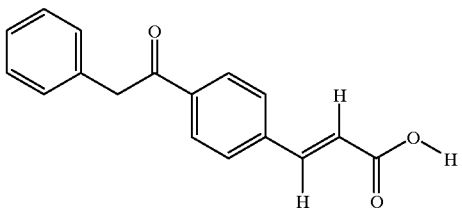

A 1 N aqueous sodium hydroxide solution (2.3 ml) and water (4 ml) are added to a solution of ethyl 4-(phenylacetyl) cinnamate (Compound No. 3-1, 675 mg) in a mixed solvent of ethanol (6 ml)-tetrahydrofuran (6 ml) under a nitrogen atmosphere, and the mixture is stirred at room temperature for 6.5 hours. To the reaction mixture is added 1 N hydrochloric acid to acidify it, and the whole is extracted with ethyl acetate. The organic layer is washed with saturated brine, dried over anhydrous magnesium sulfate and concentrated under reduced pressure. The resulting precipitate is filtered off to give 553 mg (91%) of the titled compound (Compound No. 4-1) as crystals.

(Compound No. 4-1)

mp 232–236° C. (decomp.)

IR (KBr, cm$^{-1}$) 3036, 2589, 1684, 1630, 1337, 1230, 993

The following compounds are obtained by a method similar to Example 4.

4-(n-Butyryl)cinnamic acid (Compound No. 4-2)
mp 204–210° C. (decomp.)
IR (KBr, cm$^{-1}$) 2965, 1689, 1630, 1601, 1560, 992
α-Methyl-4-(phenylacetyl)cinnamic acid (Compound No. 4-3)
mp 148.0–149.3° C.
IR (KBr, cm$^{-1}$) 2968, 1685, 1621, 1409, 1266, 728
β-Methyl-4-(phenylacetyl)cinnamic acid (Compound No. 4-4)
mp 143–149° C.
IR (KBr, cm$^{-1}$) 2898, 1684, 1623, 1559, 1499
4-Propionylcinnamic acid (Compound No. 4-5)
4-Isovalerylcinnamic acid (Compound No. 4-6)
4-Acetylcinnamic acid (Compound No. 4-7)

EXAMPLE 5

Diethyl 2-[4-[(1RS)-1-hydroxy-2-phenylethyl]phenyl] maleate (Compound No. 5-1)

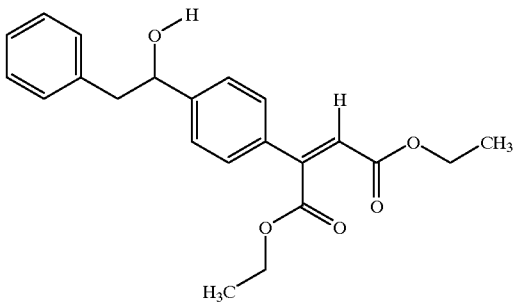

A 2.0 M solution of benzylmagnesium chloride in tetrahydrofuran (0.45 ml) is added dropwise to a solution of diethyl 2-(4-formylphenyl)maleate (Reference compound No. 4-1, 250 mg) in anhydrous tetrahydrofuran (4.5 ml) under a nitrogen atmosphere and dry ice cooling with stirring. Ten minutes after completing the addition, the mixture is stirred at room temperature for one hour. A saturated aqueous ammonium chloride solution is added to the reaction mixture, and the whole is extracted with ether. The organic layer is washed with water and saturated brine successively, dried over anhydrous magnesium sulfate and concentrated under reduced pressure. The resulting residue is purified by silica gel column chromatography to give 100 mg (30%) of the titled compound (Compound No. 5-1).

(Compound No. 5-1)

IR (Film, cm$^{-1}$) 3512, 2983, 1719, 1624, 1372, 1342, 1290, 1180, 1032, 701

EXAMPLE 6

Diethyl 2-[4-(phenylacetyl)phenyl]maleate (Compound No. 6-1)

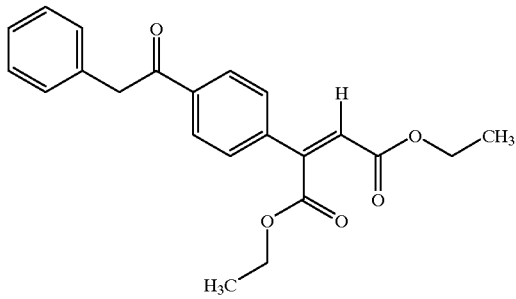

Triethylamine (0.53 ml) is added to a solution of diethyl 2-[4-[(1RS)-1-hydroxy-2-phenylethyl]phenyl]maleate (Compound No. 5-1, 280 mg) in dimethyl sulfoxide (3 ml) at room temperature with stirring, and further a solution of a sulfur trioxide-pyridine complex (484 mg) in dimethyl sulfoxide (5 ml) is added thereto. The mixture is stirred at room temperature for 2.5 hours, 0.1 N hydrochloric acid (50 ml) is added to the reaction mixture, and the whole is extracted with ether. The organic layer is washed with water and saturated brine successively, dried over anhydrous magnesium sulfate and concentrated under reduced pressure. The precipitate is filtered off to give 85 mg (31%) of the titled compound (Compound No. 6-1) as crystals.

(Compound No. 6-1)

mp 111–120° C.

IR (KBr, cm$^{-1}$) 2985, 1716, 1691, 1627, 1412, 1374, 1183, 1024, 728

EXAMPLE 7

2-[4-(Phenylacetyl)phenyl]maleic acid (Compound No. 7-1)

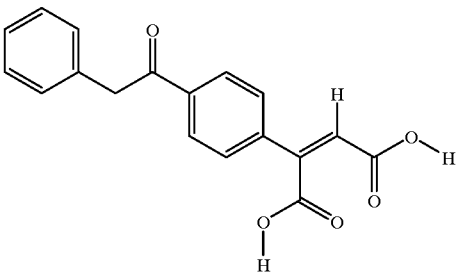

Into a pressure tube is introduced a solution of diethyl 2-[4-(phenylacetyl)phenyl]maleate (Compound No. 6-1, 80 mg) in dioxane (3 ml), concentrated hydrochloric acid (2 ml) is added thereto, and the mixture is stirred at 120° C. for one hour. The reaction mixture is concentrated under reduced pressure to give 90 mg (quantitatively) of the titled compound (Compound No. 7-1).

EXAMPLE 8

4-[2-(2,3,4,5,6-Pentafluorophenyl)acryloyl]cinnamic acid (Compound No. 8-1)

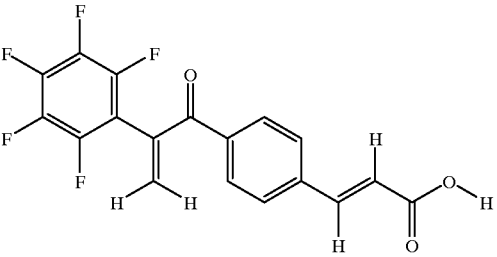

Into a pressure tube is introduced a solution of 4-[(2,3,4,5,6-pentafluorophenyl)acetyl]cinnamic acid (Compound No. 2-1, 230 mg) in dioxane (13 ml). To the solution are added paraformaldehyde (78 mg), dimethylamine hydrochloride (210 mg), acetic acid (one drop) and anhydrous magnesium sulfate (q.s.), and the mixture is stirred overnight while heating it at 130° C. Under ice cooling, 0.1 N hydrochloric acid is added to the reaction mixture to acidify it, and the whole is extracted with ethyl acetate. The organic layer is washed with saturated brine, dried over anhydrous magnesium sulfate and concentrated under reduced pressure. The precipitate is filtered off to give 222 mg (93%) of the titled compound (Compound No. 8-1) as crystals.

(Compound No. 8-1)

mp 218–220° C.

IR (KBr, cm$^{-1}$) 2837, 1691, 1668, 1518, 1494, 1283, 994

The following compounds are obtained by a method similar to Example 8.

4-[2-(4-Nitrophenyl)acryloyl]cinnamic acid (Compound No. 8-2)

mp 224.2–225.5° C.

IR (KBr, cm$^{-1}$) 2841, 1689, 1656, 1508, 1426, 1344, 1313, 848

4-[2-(4-Biphenylyl)acryloyl]cinnamic acid (Compound No. 8-3)

mp 239° C. (decomp.)

IR (KBr, cm$^{-1}$) 2989, 1688, 1655, 1632, 1601, 1562, 982

4-[2-(4-Tolyl)acryloyl]cinnamic acid (Compound No. 8-4)

4-[2-(4-Fluorophenyl)acryloyl]cinnamic acid (Compound No. 8-5)

4-[2-(4-Chlorophenyl)acryloyl]cinnamic acid (Compound No. 8-6)

4-(2-Phenylacryloyl)cinnamic acid (Compound No. 8-7)
mp 175.3–177.8° C.
IR (KBr, cm$^{-1}$) 2969, 1690, 1667, 1631, 1600, 1561, 1493, 1412, 914, 858

4-(2-Ethylacryloyl)cinnamic acid (Compound No. 8-8)
mp 174.5–175.0° C.
IR (KBr, cm$^{-1}$) 2968, 1689, 1650, 1627, 1601, 1561, 989

α-Methyl-4-(2-phenylacryloyl)cinnamic acid (Compound No. 8-9)
mp 134.5–136.5° C.
IR (KBr, cm$^{-1}$) 2966, 1666, 1600, 1414, 1265, 1215, 980

β-Methyl-4-(2-phenylacryloyl)cinnamic acid (Compound No. 8 -10)
mp 116.2–118.8° C.
IR (KBr, cm$^{-1}$) 2924, 1684, 1627, 1600, 1495, 1415, 981, 855

4-(2-Methylacryloyl)cinnamic acid (Compound No. 8-11)

4-(2-Isopropylacryloyl)cinnamic acid (Compound No. 8-12)

4-Acryloylcinnamic acid (Compound No. 8-13)

2-[4-(2-Phenylacryloyl)phenyl]maleic acid (Compound No. 8-14)
IR (Film, cm$^{-1}$) 2928, 1769, 1718, 1622, 1416, 1226, 1123, 759

EXAMPLE 9

Ethyl 4-[(2RS, 3RS)-3-hydroxy-2-phenylbutyryl]cinnamate (Compound No. 9-1)

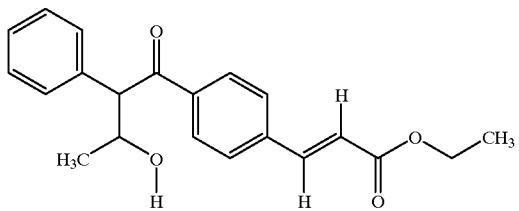

Ethyl 4-(phenylacetyl)cinnamate (Compound No. 3-1, 2.0 g) is dissolved in a mixed solvent of ethanol (14 ml)-tetrahydrofuran (34 ml). To the solution are added water (14 ml), acetaldehyde (1.9 ml) and potassium carbonate (1.9 g), and the mixture is stirred at room temperature for three hours. To the reaction mixture is added 1 N hydrochloric acid to acidify it, and the whole is extracted with ethyl acetate. The organic layer is washed with saturated brine, dried over anhydrous magnesium sulfate and concentrated under reduced pressure. The resulting residue is purified by silica gel column chromatography to give 1.75 g (76%) of the titled compound (Compound No. 9-1).

(Compound No. 9-1)

IR (Film, cm$^{-1}$) 3484, 2977, 1712, 1677, 1637, 1603, 1562, 1492, 1312, 1209, 1177

EXAMPLE 10

Ethyl 4-[(2RS, 3RS)-3-(mesyloxy)-2-phenylbutyryl]cinnamate (Compound No. 10-1)

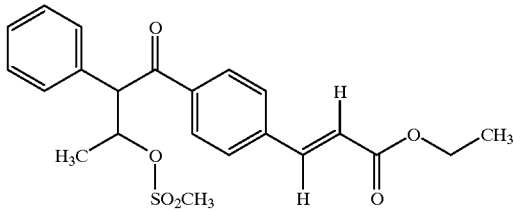

Triethylamine (1.05 ml) and mesyl chloride (0.6 ml) are added to a solution of ethyl 4-[(2RS, 3RS)-3-hydroxy-2-phenylbutyryl]cinnamate (Compound No. 9-1, 1.70 g) in anhydrous methylene chloride (25 ml) under ice cooling, and the mixture is stirred for 2.5 hours. A 10% aqueous citric acid solution is added to the reaction mixture to acidify it, and the whole is extracted with ether. The organic layer is washed with water and saturated brine successively, dried over anhydrous magnesium sulfate and concentrated under reduced pressure to give 1.75 g (84%) of the titled compound (Compound No. 10-1).

(Compound No. 10-1)

IR (Film, cm$^{-1}$) 3030, 1713, 1681, 1353, 1174, 906

EXAMPLE 11

Ethyl 4-[(E, Z)-2-phenyl-2-butenoyl]cinnamate (Compound No. 11-1)

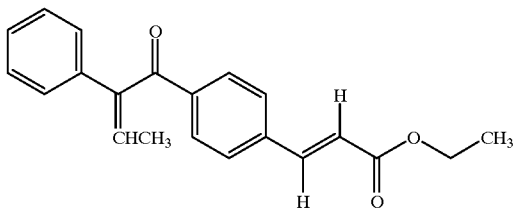

1,8-Diazabicyclo[5.4.0]-7-undecene (0.32 ml) is added to a solution of ethyl 4-[(2RS, 3RS)-3-(mesyloxy)-2-phenylbutyryl]cinnamate (Compound No. 10-1, 800 mg) in tetrahydrofuran (10 ml), and the mixture is stirred at room temperature for one hour. A 10% aqueous citric acid solution is added to the reaction mixture to acidify it, and the whole is extracted with ether. The organic layer is washed with water and saturated brine successively, dried over anhydrous magnesium sulfate and concentrated under reduced pressure. The resulting oily matter is purified by silica gel column chromatography to give 535 mg (87%) of the titled compound (Compound No. 11-1).

(Compound No. 11-1)

IR (Film, cm$^{-1}$) 2980, 1713, 1639, 1602, 1366, 1312, 1270, 1204, 1175

EXAMPLE 12

4-[(E, Z)-2-Phenyl-2-butenoyl]cinnamic acid (Compound No. 12-1)

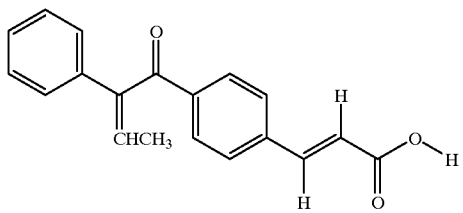

Ethyl 4-[(E, Z)-2-phenyl-2-butenoyl]cinnamate (Compound No. 11-1, 260 mg) is dissolved in a mixed solvent of tetrahydrofuran (4 ml)-ethanol (4 ml). To the solution are added water (3 ml) and 1N aqueous sodium hydroxide solution (0.32 ml), an the mixture is stirred at room temperature for 4.5 hours. To the reaction mixture is added 1N hydrochloric acid to acidify it, and the whole is extracted with ethyl acetate. The organic layer is washed with saturated brine, dried over anhydrous magnesium sulfate and concentrated under reduced pressure. The precipitate is filtered off to give 115 mg (49%) of the titled compound (Compound No. 12-1) as crystals.
(Compound No. 12-1)
mp 153–156° C.
IR (KBr, $cm^{-1}$) 2974, 1690, 1630, 1425, 1265, 700

EXAMPLE 13 t-Butyl 4-(3, 3-difluoro-2-phenylacryloyl)cinnamate (Compound No. 13-1)

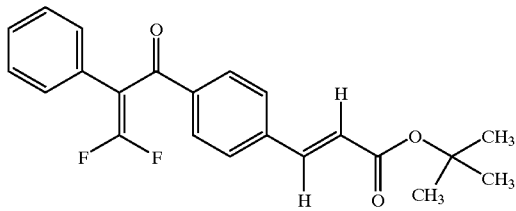

N-Methylmorpholine (0.29 ml) is added to a solution of t-butyl 4-carboxycinnamate (Reference compound No. 2-3, 1.9 g) in anhydrous tetrahydrofuran (38 ml) under a nitrogen atmosphere and ice-salt refrigerant cooling. Then, isobutyl chloroformate (0.99 ml) is added dropwise to the solution, and the mixture is stirred for 16 minutes to give the corresponding mixed acid anhydride.

A 1.6 M solution of n-butyllithium in exane (10 ml) is added dropwise to a solution of 2, 2, 2-trifluoroethyl tosylate (1.95 g) in anhydrous tetrahydrofuran (18 ml) under a nitrogen atmosphere and dry ice cooling, and the mixture is stirred for 35 minutes. Then, a solution of triphenylborane (2.0 g) in anhydrous tetrahydrofuran (20 ml) is added dropwise to the mixture under dry ice cooling, and the whole is stirred under dry ice cooling for one hour and further at room temperature for three hours. To the reaction mixture are added hexamethylphosphoramide (12 ml) and copper(I) iodide (2.9 g) under ice cooling, and the mixture is stirred for 45 minutes. Then, the above-mentioned mixed acid anhydride solution is added dropwise to the mixture, stirring it at room temperature overnight. A 10% aqueous citric acid solution is added to the reaction mixture to acidify it, and the whole is extracted with ether. The organic layer is washed with water and saturated brine successively, dried over anhydrous magnesium sulfate and concentrated under reduced pressure. The resulting oily matter is purified by silica gel column chromatography to give 442 mg (16%) of the titled compound (Compound No. 13-1).
(Compound No. 13-1)
mp 88–94° C.
IR (KBr, $cm^{-1}$) 3006, 1740, 1709, 1637, 1608, 1569, 1271, 1192, 1151

EXAMPLE 14

4-(3, 3-Difluoro-2-phenylacryloyl)cinnamic acid (Compound No. 14-1)

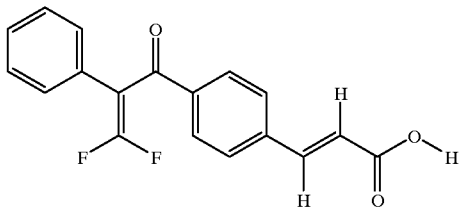

t-Butyl 4-(3, 3-difluoro-2-phenylacryloyl)cinnamate (Compound No. 13-1, 302 mg) is dissolved in a 4N solution of hydrogen chloride in dioxane (2.45 ml) under a nitrogen atmosphere, and the solution is stirred at room temperature for 19.5 hours. Ether is added to the reaction mixture, and the resulting precipitate is filtered off to give 116 mg (45%) of the titled compound (Compound No. 14-1).
(Compound No. 14-1)
mp 235–248° C.
IR (KBr, $cm^{-1}$) 2833, 1724, 1689, 1631, 1605, 1569, 1278, 922

EXAMPLE 15

Monoethyl (E)-2-[4-(phenylacetyl)phenyl]vinylphosphonate Compound No. 15-1)

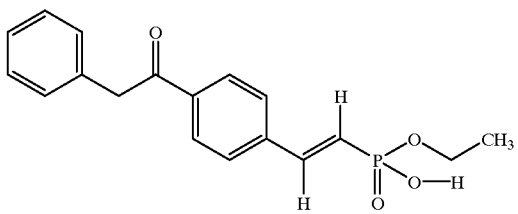

Thionyl chloride (5.0 ml) is added dropwise to a solution of diethyl (E)-2-(4-carboxyphenyl)vinylphosphonate (Reference compound No. 5-1, 3.27 g) in chloroform (5 ml), then dimethylformamide (one drop) is added to the solution, and the mixture is refluxed for 24 hours. The reaction mixture is concentrated under reduced pressure to give the corresponding acid chloride.

To anhydrous 1, 2-dimethoxyethane (33 ml) are added activated zinc (1.6 g) and a palladium(II) chloride-bis (triphenylphosphine) complex (0.89 g) under a nitrogen atmosphere, and benzyl bromide (1.5 ml) is added dropwise thereto under ice cooling with stirring. Further, a solution of the above-mentioned acid chloride in anhydrous 1, 2-dimethoxyethane (25 ml) is added dropwise thereto, and the mixture is stirred at room temperature for three days. The reaction mixture is filtered with Celite, and the filtrate is concentrated under reduced pressure. To the concentrate is added 1N hydrochloric acid, and the whole is extracted with ethyl acetate. The organic layer is washed with saturated brine, dried over anhydrous sodium sulfate and concentrated under reduced pressure. The resulting residue is purified by silica gel column chromatography to give 1.96 g (52%) of the titled compound (Compound No. 15-1).
(Compound No. 15-1)
IR (Film, cm$^{-1}$) 3030, 1681, 1603, 1561, 1496, 1454, 1269, 1200, 945

EXAMPLE 16

Monoethyl (E)-2-[4-(2-phenylacryloyl) phenyl] vinylphosphonate (Compound No. 16-1)

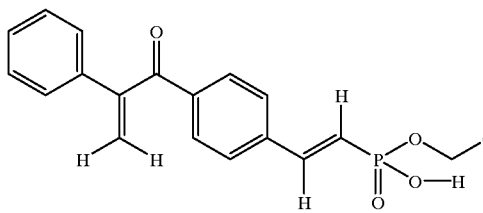

Into a pressure tube is introduced a solution of monoethyl (E)-O2-[4-(phenylacetyl)phenyl]vinylphosphonate (Compound No. 15-1, 1.96 g) in dioxane (11 ml). To the solution are added paraformaldehyde (0.66 g), dimethylamine hydrochloride (1.8 g), acetic acid (one drop) and anhydrous magnesium sulfate (q.s.), and the mixture is stirred for five hours while heating it at 130° C. Under ice cooling, 1N hydrochloric acid is added to the reaction mixture to acidify it, and the whole is extracted with ethyl acetate. The organic layer is washed with saturated brine, dried over anhydrous sodium sulfate and concentrated under reduced pressure. The resulting oily matter is purified by silica gel column chromatography to give 0.55 g (29%) of the titled compound (Compound No. 16-1).
(Compound No. 16-1)
IR (Film, cm$^{-1}$) 2983, 2904, 1719, 1665, 1618, 1410, 1214, 984, 856, 833

EXAMPLE 17

(E)-2-[4-(2-Phenylacryloyl)phenyl]vinylphosphonic acid (Compound No. 17-1)

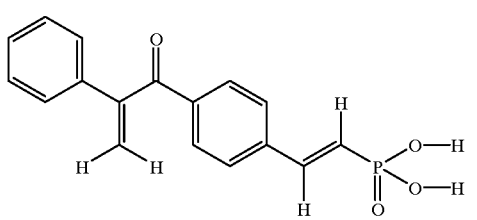

Bromotrimethylsilane (0.28 ml) is added dropwise to a solution of monoethyl (E)-2-[4-(2-phenylacryloyl) phenyl] vinylphosphonate (Compound No. 16-1, 180 mg) in anhydrous methylene chloride (1.3 ml) under a nitrogen atmosphere at room temperature, and the mixture is stirred for one hour. Ethyl acetate is added to the reaction mixture. The organic layer is washed with water and saturated brine successively, dried over anhydrous sodium sulfate and concentrated under reduced pressure.

The resulting oily matter is dissolved in methylene chloride (4.7 ml), triethylamine (0.20 ml) is added to the solution, and the mixture is stirred at room temperature for one hour. Ethyl acetate is added to the reaction mixture. The organic layer is washed with 0.1N hydrochloric acid and saturated brine successively, dried over anhydrous sodium sulfate and concentrated under reduced pressure. The precipitate is filtered off to give 22 mg (13%) of the titled compound (Compound No. 17-1) as crystals.
(Compound No. 17-1)
mp 137–147° C.
IR (KBr, cm$^{-1}$) 3025, 1654, 1602, 1495, 1409, 1216, 929

Formulation

Formulation examples of eyedrops and oral preparation using the present compound are shown below.

| 1) Eyedrops Formulation 1 in 10 ml | |
|---|---|
| Present compound | 1 mg |
| Concentrated glycerin | 250 mg |
| Polysorbate 80 | 200 mg |
| Sodium dihydrogenphosphate dihydrate | 20 mg |
| 1 N Sodium hydroxide | q.s. |
| 1 N Hydrochloric acid | q.s. |
| Sterile purified water | q.s. |
| 2) Tablet Formulation 1 in 100 mg | |
| Present compound | 1 mg |
| Lactose | 66.4 mg |
| Cornstarch | 20 mg |
| Calcium carboxymethylcellulose | 6 mg |
| Hydroxypropylcellulose | 6 mg |
| Magnesium stearate | 0.6 mg |

Pharmacological Test

In order to study utility of the present compounds to glaucoma, 1) effects on morphology of trabecular meshwork cells, 2) intraocular pressure-lowering effects by anterior chamber administration and 3) intraocular pressure-lowering effects by instillation using laser-induced high intraocular pressure animal models were investigated.

1) Effects on Morphology of Trabecular Meshwork Cells

A possibility has been reported that drugs having effects of increasing aqueous humor outflow can be found by evaluating effects of drugs on morphology of cultured trabecular meshwork cells (Invest. Ophthalmol. Vis. Sci., 33, 2631–2640 (1992)). Accordingly, effects of the present compounds on morphology of bovine cultured trabecular meshwork cells were studied in the similar manner to the method described in the above-mentioned literature.

Experimental Method

Morphological changes in bovine cultured trabecular meshwork cells by adding the present compounds were quantitatively evaluated by image analysis.

Preparation of Cells

Bovine trabecular meshwork cells (passage number 1 to 5) cultured in a basal medium for mammalian cell culture d-MEM (Dulbecco's Modified Eagle Medium, manufactured by Gibco Co., Ltd.) containing fetal bovine serum (10%), amphotericin B (2.5 μg/ml) and gentamicin (50 μg/ml) were treated with a trypsin-EDTA solution (0.05% trypsin, 0.53 mM EDTA·4 Na) 24 hours before the later drug treatment and seeded in a 24-well plate ($10^4$ cells/well). Twelve hours before the later drug treatment, the cells were washed with phosphate-buffered physiological saline, and then the medium was replaced by D-MEM containing amphotericin B (2.5 μg/ml) and gentamicin (50 μg/ml) (hereinafter referred to as "medium A"). One hour before the later drug treatment, cells which did not contact each other were selected from the cells prepared as mentioned above and used for experiment.

Preparation of Test Compound Solution

A test compound was dissolved in dimethyl sulfoxide (DMSO), and the medium A was added to the solution, followed by sterilizing the solution by filtration. The medium A was further added to the solution to dilute it at a prescribed concentration. This diluted solution was maintained isothermally under a 5% carbon dioxide gas atmosphere at 37° C. for one hour, from one hour before the later drug treatment to prepare a test compound solution.

Method of Measurement

First, cells were photographed using a well-scanner one hour before the drug treatment. Next, the medium of the cells was replaced by the test compound solution, and the cells were treated with the drug and incubated under a 5% carbon dioxide gas atmosphere at 37° C. for three hours. Then, the same cells as those photographed one hour before the drug treatment were photographed using the well-scanner.

Image Analysis

Photographed cell images were incorporated from the photographs into an image analysis system with a CCD camera (manufactured by HAMAMATU Co., Ltd.). Outlines of the incorporated cell images were traced, and areas were measured.

Degrees of the morphological changes made by the test compounds on the trabecular meshwork cells are expressed by the following rates of changes in areas (%).

Rate of change in area (%)=[(A−B)/A]×100

A: Cell area before drug treatment

B: Cell area after drug treatment

Results

Table 1 shows concentrations required to reduce the cell area of the trabecular meshwork cells by 50%, i.e, $EC_{50}$, as examples of test results. Table 1 shows also a result using ethacrynic acid as a control drug.

TABLE 1

| Test compound | $EC_{50}$ (M) |
| --- | --- |
| Compound No. 8-1 | $6.6 \times 10^{-7}$ |
| Compound No. 8-2 | $1.7 \times 10^{-6}$ |
| Compound No. 8-7 | $8.1 \times 10^{-7}$ |
| Compound No. 8-9 | $3.9 \times 10^{-6}$ |
| Compound No. 8-10 | $2.9 \times 10^{-6}$ |
| Ethacrynic acid | $6.2 \times 10^{-5}$ |

As shown in Table 1, the present compounds were recognized to have excellent cell morphological change effects on the trabecular meshwork cells. These effects were over ten times higher than that of ethacrynic acid, which was a well-known comparative control drug.

2) Intraocular Pressure-Lowering Effects by Anterior Chamber Administration

A method of evaluating intraocular pressure-lowering effects of the drugs by administering them into anterior chambers of cynomolgus monkeys has been reported (Am. J. Ophthalmol., 113, 706–711 (1992)). Accordingly, effects of the present compound on intraocular pressure were studied in the similar manner to the method described in the above-mentioned literature.

Experimental Method

Experimental Animals

Healthy male cynomolgus monkeys weighing 4.0 to 7.0 kg and being four to seven years old were used as experimental animals.

Preparation of Test Compound Solution

A test compound to be used was dissolved in dimethyl sulfoxide (DMSO), and then phosphate-buffered physiological saline was added to the solution to dilute it at a prescribed concentration ($10^{-3}$M, 1% DMSO), followed by sterilizing the solution by filtration to prepare a test compound solution.

Method of Administering Drugs

The test compound solution (10 $\mu$l) was administered with a micro syringe and a 30G needle into an anterior chamber of one eye of a cynomolgus monkey anesthetized generally by administering ketamine hydrochloride (5 to 10 mg/kg) intramuscularly. Only vehicle was administered into the other eye.

Method of Measurement

The intraocular pressure was measured with an applanation tonometer immediately before and prescribed periods after administering the test compound. Before measuring the introcular pressure, the cynomolgus monkey was anesthetized generally with ketamine hydrochloride (5 to 10 mg/kg), and then one drop of a 0.4% oxybuprocaine hydrochloride eyedrops, which is a local anesthetic, was instilled into the cynomolgus monkey.

Results

An effect of the test compound on the intraocular pressure exhibited (t) hours after administering the test compound is expressed by the following intraocular pressure-lowering value (mmHg).

Intraocular pressure-lowering value (mmHg)=[IOP(V−t)−IOP (D−t)]−[IOP(V−0)−IOP(D−0)]

IOP(D−t): Intraocular pressure of the eye into which the test compound was administered, measured (t) hours after administering the test compound IOP(D−0): Intraocular pressure of the eye into which the test compound was administered, measured immediately before administering the test compound IOP(V−t): Intraocular pressure of the eye into which the vehicle was administered, measured (t) hours after administering the vehicle IOP(V−0): Intraocular pressure of the eye into which the vehicle was administered, measured immediately before administering the vehicle Table 2 shows a maximum intraocular pressure-lowering value (mmHg) after injecting the test compound solution (Compound No. 8-7) into the anterior chamber as one example of a test result. Table 2 shows also a result using ethacrynic acid as a control drug.

TABLE 2

| | Compound No. 8-7*) | Ethacrynic acid**) |
| --- | --- | --- |
| Maximum intraocular pressure-lowering value (mmHg) | 7.0 | 2.0 |

*)The value is an average value of six samples.
**)The value is an average value of five samples.

As shown in Table 2, the present compound exhibited an excellent intraocular pressure-lowering effect. The present compound exhibited also a higher intraocular pressure-lowering effect than ethacrynic acid, which was a comparative control drug.

3) Intraocular Pressure-Lowering Effects by Instillation Using Laser-Induced High Intraocular Pressure Animal Models A method of evaluating intraocular pressure-lowering effects of the drugs by instilling them into laser-induced high intraocular pressure monkey models has been reported (Arch. Opththalmol., 105, 249–252 (1987)). Accordingly, intraocular pressure-lowering effects by instilling the present compound were studied in the similar manner to the method described in the above-mentioned literature.

Experimental Method

Experimental Animals

Male cynomolgus monkeys weighing 5 to 6 kg were used for experiment. Five eyes of four monkeys of which intraocular pressure had been elevated by irradiating trabecular meshwork of the monkeys at 100 to 150 spots every one week with an argon laser (Coherent Radiation, Models 800) were used. Laser irradiation conditions were set at 1000 mW and 0.2 sec.

Preparation of Test Compound Solution

A test compound was dissolved in purified water, then concentrated glycerin and sodium chloride were added to the solution to adjust osmotic pressure to 1, and 0.1 M aqueous sodium hydroxide solution was added thereto to adjust pH to 7.4 and to prepare a 0.3% solution. Then, the solution was sterilized by filtration to prepare a test compound solution.

Method of Administering Drugs

First, in order to study effects of a vehicle on intraocular pressure, only vehicle was instilled twice a day (at 10 a.m. and 5 p.m.) for one week continuously. Then, the test compound solution was instilled twice a day (at 10 a.m. and 5 p.m.) for one week continuously.

Method of Measurement

Intraocular pressure was measured with an applanation tonometer before administering the drug and a prescribed period after the instillation. Chlorpromazine (1 mg/kg) was administered intramuscularly to the cynomolgus monkey one hour before the measurement to sedate the monkey, one drop of a 0.4% oxybuprocaine hydrochloride eyedrops, which is a local anesthetic, was instilled into the monkey, and then the intraocular pressure was measured.

Results

Effects of the test compound solution on intraocular pressure exhibited six hours after the morning instillation are expressed by intraocular pressure change differences (mmHg) determined by the following equation.

Intraocular pressure change difference (mmHg)=[IOP(D-6)-IOP(D-0)]-[IOP(V-6)-IOP(V-0)]

IOP(D-6): Intraocular pressure measured six hours after the morning instillation of the test compound solution IOP(D-0): Intraocular pressure measured before administering the test compound solution IOP(V-6): Intraocular pressure measured six hours after the morning instillation of the vehicle IOP(V-0): Intraocular pressure measured before administering the vehicle Table 3 shows a change with days in the intraocular pressure change difference exhibited after instilling the test compound (Compound No. 8-7) solution as one example of test results.

TABLE 3

| Intraocular pressure measurement day | (Compound No. 8-7) Intraocular pressure change difference (mmHg) |
|---|---|
| 1st day | +5.8 |
| 2nd day | -7.6 |
| 3rd day | -6.6 |
| 4th day | -1.2 |
| 5th day | -6.6 |
| 6th day | -8.6 |
| 7th day | -2.8 |

The values in the table are averages of five eyes.

As shown in Table 3, the test compound (Compound No. 8-7) exhibited an excellent intraocular pressure-lowering effect. No disorder was recognized in an anterior segment of the eye throughout all instillation periods.

From the above-mentioned results, the present compound was recognized to have the excellent intraocular pressure-lowering effect and to be useful as a therapeutic agent for glaucoma.

Industrial Applicability

The present invention provides novel compounds which are useful as therapeutic agents for glaucoma and has great applicability in an ophthalmological field.

What is claimed is:

1. A compound represented by the following general formula (I) or a salt thereof,

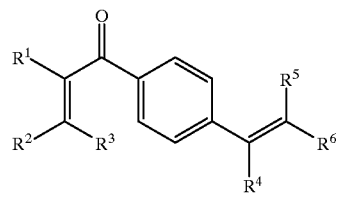

wherein $R^1$ is hydrogen, lower alkyl or substituted or unsubstituted phenyl phenyl, and the phenyl can be substituted by wherein the substituents are selected from the group consisting of lower alkyl, hydroxy, lower alkoxy, halogen, nitro or phenyl, $R^2$ and $R^3$, being the same or different, are hydrogen, halogen or lower alkyl, $R^4$ and $R^5$, being the same or different, are hydrogen, lower alkyl or carboxylic acid or carboxylic ester thereof, $R^6$ is carboxylic acid or carboxylic ester; or phosphono or ester thereof.

2. The compound or a salt thereof as claimed in claim 1, wherein $R^1$ is hydrogen, lower alky, or substituted or unsubstituted phenyl wherein the substituents are selected from the group consisting of lower alkyl, halogen, nitro and phenyl; and $R^4$ and $R^5$, being the same or different, are hydrogen, lower alkyl or carboxylic acid.

3. The compound or a salt thereof as claimed in claim 1, wherein $R^1$ is substituted or unsubstituted phenyl wherein the substituents are selected from the group consisting of halogen, nitro and phenyl;

both $R^2$ and $R^3$ are hydrogen;

$R^4$ and $R^5$, being the same or different, are hydrogen or lower alkyl; and $R^6$ is carboxylic acid.

4. The compound or a salt thereof as claimed in claim 1, wherein $R^1$ is phenyl, pentafluorophenyl, 4-nitrophenyl or 4-biphenylyl;

both $R^2$ and $R^3$ are hydrogen;

$R^4$ and $R^5$, being the same or different, are hydrogen or methyl; and $R^6$ is carboxylic acid.

5. A compound selected from the group consisting of 4-[2-(2, 3, 4, 5, 6-pentafluorophenyl)acryloyl]cinnamic acid, 4-[2-(4-nitrophenyl) acryloyl]cinnamic acid, 4-(2-phenylacryloyl)cinnamic acid, α-methyl-4-(2-phenylacryloyl)cinnamic acid and β-methyl-4-(2-phenylacryloyl) cinnamic acid or a salt thereof.

6. A pharmaceutical composition comprising the compound or a salt thereof as claimed in claim 1 as an active ingredient.

7. An aqueous humor outflow improving agent comprising the compound or a salt thereof as claimed in claim 1 as an active ingredient.

8. An intraocular pressure-lowering agent comprising the compound or a salt thereof as claimed in claim 1 as an active ingredient.

9. The compound of claim 5 selected from the group consisting of 4-[2-(2,3,4,5,6-pentafluorophenyl)acryloyl] cinnamic acid and a salt thereof.

10. The compound of claim 5 selected from the group consisting of 4-[2-(4-nitrophenyl)acryloyl]cinnamic acid and a salt thereof.

11. The compound of claim 5 selected from the group consisting of 4-(2-phenylacryloyl]cinnamic acid and a salt thereof.

12. The compound of claim 5 selected from the group consisting of α-methyl-4-(2-phenylacryloyl]cinnamic acid and a salt thereof.

13. The compound of claim 5 selected from the group consisting of β-methyl-4-(2-phenylacryloyl]cinnamic acid and a salt thereof.

* * * * *